(12) United States Patent
Hoogwater et al.

(10) Patent No.: US 11,433,321 B2
(45) Date of Patent: Sep. 6, 2022

(54) SYSTEM AND METHOD FOR REMOVING SULFUR FROM HYDROCARBON FLUIDS

(71) Applicant: BBL HOLDINGS, LLC, Aberdeen, SD (US)

(72) Inventors: Sjoerd Hoogwater, Littleton, CO (US); Tom Wilson, Buffalo, SD (US); Dan A. Johnson, Dickinson, ND (US)

( * ) Notice: Subject to any disclaimer, the term of this patent is extended or adjusted under 35 U.S.C. 154(b) by 548 days.

(21) Appl. No.: 16/252,766

(22) Filed: Jan. 21, 2019

(65) Prior Publication Data

US 2019/0255463 A1 Aug. 22, 2019

Related U.S. Application Data

(63) Continuation-in-part of application No. 14/268,382, filed on May 2, 2014, now Pat. No. 10,258,904.

(Continued)

(30) Foreign Application Priority Data

May 4, 2015 (CA) ................................ CA 2947738

(51) Int. Cl.
*C02F 3/28* (2006.01)
*B01D 19/00* (2006.01)
(Continued)

(52) U.S. Cl.
CPC ......... *B01D 19/0005* (2013.01); *C10G 29/02* (2013.01); *B01D 5/003* (2013.01);
(Continued)

(58) Field of Classification Search
CPC .............. C10G 29/02; C10G 2300/202; C10G 2300/207; C10G 2300/80; B01D 19/0005;
(Continued)

(56) References Cited

U.S. PATENT DOCUMENTS

| | | |
|---|---|---|
| 2,729,590 A | 1/1956 | Bishop |
| 3,208,930 A | 9/1965 | Andrassy |

(Continued)

FOREIGN PATENT DOCUMENTS

EP 2770041 8/2014

OTHER PUBLICATIONS

"Safe, Cost-effective Onsite Removal of H2S from Crude Oil and Produced Water", S2S, LLC, pp. 1-7, web page www.sourtosweet.net, download date May 30, 2014.

(Continued)

*Primary Examiner* — Dung H Bui
(74) *Attorney, Agent, or Firm* — Jeffrey A. Proehl; Woods, Fuller, Shultz & Smith, PC

(57) ABSTRACT

Systems and methods for sulfur-compound removal from hydrocarbon liquids may include at least one tank defining a chamber with top and bottom ends, a gas inlet into the chamber, a gas outlet from the chamber, a fluid inlet into the chamber, and a fluid outlet from the chamber. A fluid circulation assembly creates a hydrocarbon liquid flow on a liquid path, and a gas circulation assembly circulates a gas flow along a gas path. The gas inlet and outlet and the fluid inlet and outlet of the tank may be arranged to create a crossflow and counterflow of the liquid and gas flows in the chamber of the tank such that sulfur-containing compounds are transferred from the liquid to the gas flow. A gas processor assembly may remove sulfur-containing compounds from the gas flow before recirculating the gas flow. The gas flow may be predominantly nitrogen (N2) gas.

11 Claims, 9 Drawing Sheets

Related U.S. Application Data

(60) Provisional application No. 62/619,429, filed on Jan. 19, 2018, provisional application No. 61/860,051, filed on Jul. 30, 2013.

(51) Int. Cl.
  *C10G 29/02* (2006.01)
  *B01D 5/00* (2006.01)
  *B01D 53/14* (2006.01)
  *B01D 53/18* (2006.01)
  *B01D 53/48* (2006.01)
  *B01D 53/52* (2006.01)
  *B01D 17/00* (2006.01)
  *C07C 7/00* (2006.01)

(52) U.S. Cl.
  CPC ............ *B01D 5/006* (2013.01); *B01D 5/0027* (2013.01); *B01D 17/00* (2013.01); *B01D 19/00* (2013.01); *B01D 53/1431* (2013.01); *B01D 53/1462* (2013.01); *B01D 53/1468* (2013.01); *B01D 53/18* (2013.01); *B01D 53/185* (2013.01); *B01D 53/48* (2013.01); *B01D 53/485* (2013.01); *B01D 53/52* (2013.01); *C07C 7/005* (2013.01); *C10G 2300/202* (2013.01); *C10G 2300/207* (2013.01); *C10G 2300/80* (2013.01)

(58) Field of Classification Search
  CPC ...... B01D 17/00; B01D 5/0027; B01D 5/003; B01D 5/006; B01D 53/1431; B01D 53/1462; B01D 53/1468; B01D 53/18; B01D 53/185; B01D 53/48; B01D 53/485; B01D 53/52; B01D 53/523; B01D 53/526; B01D 53/38; B01D 53/40; B01D 53/44; C07C 7/005
  See application file for complete search history.

(56) References Cited

U.S. PATENT DOCUMENTS

| | | | | |
|---|---|---|---|---|
| 3,691,732 | A | 9/1972 | Richards | |
| 3,822,341 | A | 7/1974 | Smith | |
| 5,023,064 | A | 6/1991 | Burgess | |
| 5,171,334 | A * | 12/1992 | Kabis | B01D 19/0005 210/170.07 |
| 5,387,344 | A | 2/1995 | Mccombs | |
| 5,389,126 | A * | 2/1995 | Baker | B01D 19/0005 95/258 |
| 5,405,435 | A | 4/1995 | Bekedam | |
| 5,415,681 | A * | 5/1995 | Baker | B01D 19/0005 95/246 |
| 6,080,320 | A | 6/2000 | Von Phul | |
| 6,123,750 | A | 9/2000 | Espinal | |
| 6,306,288 | B1 | 10/2001 | Pittman | |
| 7,678,263 | B2 | 3/2010 | Mock | |
| 9,364,773 | B2 | 6/2016 | Morris | |
| 2004/0178152 | A1 | 9/2004 | Morse | |
| 2007/0175796 | A1 | 8/2007 | Mock | |
| 2008/0174033 | A1 | 7/2008 | Duesel | |
| 2008/0267847 | A1 | 10/2008 | Gal | |
| 2012/0273339 | A1 | 11/2012 | Lee | |
| 2012/0273393 | A1 | 11/2012 | Whyatt | |
| 2013/0026062 | A1 | 1/2013 | Al-Shahrani | |
| 2013/0310468 | A1 | 11/2013 | Greer | |
| 2014/0238902 | A1 | 8/2014 | Morris | |
| 2015/0315485 | A1 * | 11/2015 | Morris | B01D 19/0005 95/8 |
| 2017/0072337 | A1 * | 3/2017 | Wilson | B01D 19/0005 |

OTHER PUBLICATIONS

"Treat Sour Oil and Water Safely with the S2S Hydrogen Sulfide Removal Technology", brochure, Sour to Sweet, Denver, CO, date unknown.

* cited by examiner

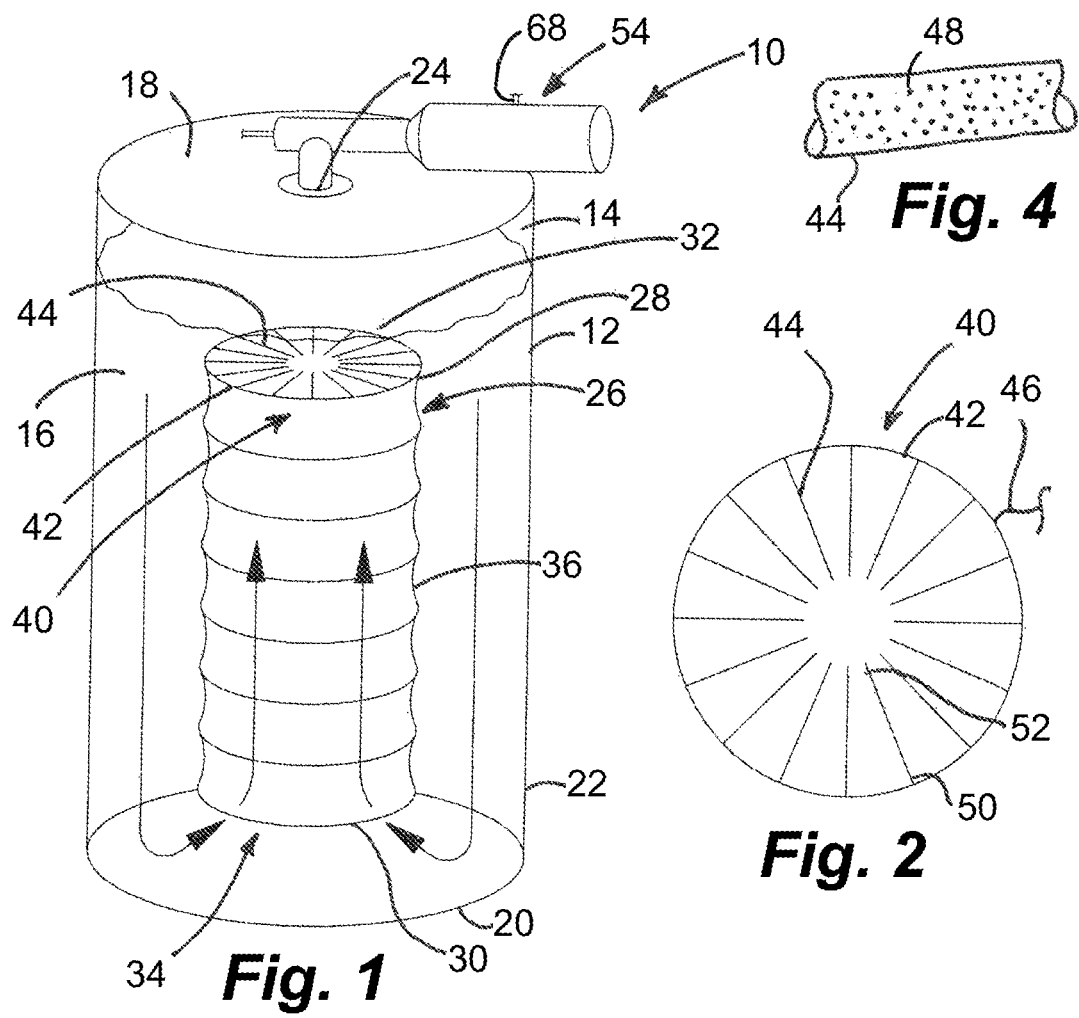
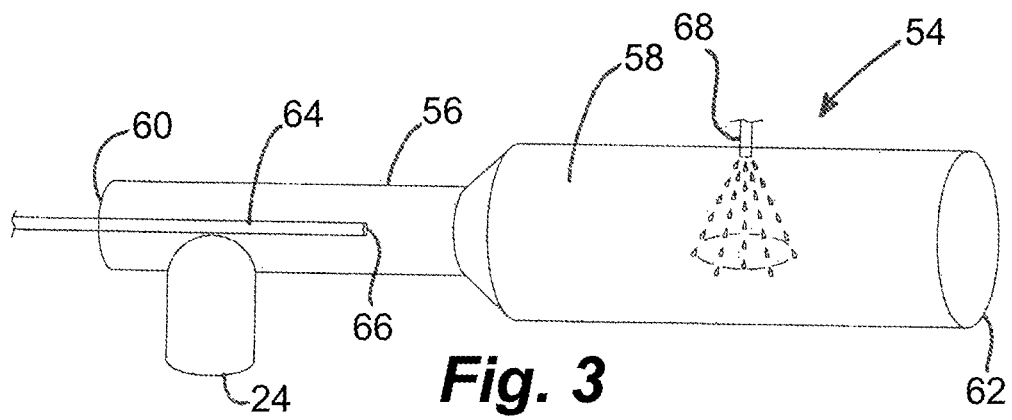

SYSTEM AND METHOD FOR REMOVING SULFUR FROM HYDROCARBON FLUIDS

REFERENCE TO RELATED APPLICATIONS

This application is a continuation in part of U.S. patent application Ser. No. 14/268,382, filed May 2, 2014; and claims the priority of U.S. provisional patent application No. 61/860,051, filed Jul. 30, 2013, and U.S. provisional patent application no. 62/619,429, filed Jan. 19, 2018, all of which are incorporated by reference in their entireties.

BACKGROUND

Field

The present disclosure relates to methods and systems for removing substances such as sulfur and sulfur-containing compounds from hydrocarbon compounds, and more particularly pertains to a new system and method for removing sulfur from hydrocarbon fluids that can be performed in a relatively simple and inexpensive manner.

SUMMARY

In some aspects, the present disclosure relates to an apparatus for removing sulfur from a hydrocarbon liquid, and may comprise a tank having an interior defining a chamber configured to hold a liquid, with the tank including an upper wall and a lower wall. The apparatus may also comprise a barrier in the chamber forming at least a partial barrier to liquid flow in the chamber, with at least a portion of the barrier extending substantially vertically in the chamber and a gap being defined between the lower wall of the tank and a lower portion of the barrier. The apparatus may further include a gas distribution manifold for introducing the gas into the liquid and being positioned in the chamber for being submerged in liquid positioned in the chamber. At least a portion of the gas distribution manifold may be perforated with holes to permit gas in an interior of the manifold to exit the manifold. The apparatus may also comprise a gas conversion structure defining an interior in fluid communication with the chamber of the tank. The gas conversion structure may include a conversion tube defining a tube interior and having an inlet end and an outlet end, with the tube interior being in fluid communication with the chamber of the tank, and an air injection device configured to inject air into the tube interior of the conversion tube and draw gas from the chamber of the tank. The gas conversion structure may also include a water injection device configured to inject water into the tube interior of the injection tube to create a mist of water in the tube interior to contact the gas from the chamber of the tank, and a fluid drain configured to drain fluid from the tube interior.

In other aspects, the present disclosure relates to an apparatus for removing sulfur-containing compounds from a hydrocarbon liquid. The apparatus may comprise at least one tank defining a chamber with a top end and a bottom end, a gas inlet toward the bottom end of the chamber and through which a gas is introduced into the chamber, a gas outlet toward the top end of the chamber and through which a gas exits the chamber, a fluid inlet toward the top end of the chamber and through which the hydrocarbon fluid is introduced into the chamber, and a fluid outlet toward the bottom end and through which the hydrocarbon fluid exits the chamber. The apparatus may also include a fluid circulation assembly with at least one pump in fluid communication with the fluid inlet of the at least one tank to create a flow of the hydrocarbon liquid into the chamber to descend from the fluid input to the fluid outlet, and a gas circulation assembly including a gas compressor configured to circulate a gas flow along a gas path and from the gas inlet of the tank to the gas outlet of the tank. The gas flow may be predominantly nitrogen (N2) gas. The gas inlet and outlet and the fluid inlet and outlet of the at least one tank may be arranged on the tank to create a crossflow of the liquid flow and the gas flow in the chamber of the tank to facilitate transfer of sulfur-containing compounds from the liquid flow to the gas flow. The apparatus may also include a gas processor assembly configured to remove sulfur-containing compounds from the gas flow before recirculating the gas flow through the chamber of the at least one tank.

In other aspects, the disclosure relates to a method of removing sulfur from a hydrocarbon liquid may include providing a quantity of a hydrocarbon liquid in a tank with a space above the liquid, creating sulfur-containing gases from sulfur in the hydrocarbon liquid, capturing the sulfur-containing gases created, and removing sulfur from the sulfur-containing gases.

There has thus been outlined, rather broadly, some of the more important elements of the disclosure in order that the detailed description thereof that follows may be better understood, and in order that the present contribution to the art may be better appreciated. There are additional elements of the disclosure that will be described hereinafter and which will form the subject matter of the claims appended hereto.

In this respect, before explaining at least one embodiment or implementation in greater detail, it is to be understood that the scope of the disclosure is not limited in its application to the details of construction and to the arrangements of the components, as well as the particulars of the steps, set forth in the following description or illustrated in the drawings. The disclosure is capable of other embodiments and implementations and is thus capable of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present disclosure. It is important, therefore, that the claims be regarded as including such equivalent constructions insofar as they do not depart from the spirit and scope of the present disclosure.

The advantages of the various embodiments of the present disclosure, along with the various features of novelty that characterize the disclosure, are disclosed in the following descriptive matter and accompanying drawings.

BRIEF DESCRIPTION OF THE DRAWINGS

The disclosure will be better understood and when consideration is given to the drawings and the detailed description which follows. Such description makes reference to the annexed drawings wherein:

FIG. 1 is a schematic perspective view of a new system for removing sulfur from hydrocarbon fluids according to the present disclosure.

FIG. 2 is a schematic top view of an aspect of the system including a gas distribution manifold, according to an illustrative embodiment.

FIG. 3 is a schematic perspective view of an aspect of the system including a gas conversion structure, according to an illustrative embodiment.

FIG. 4 is a schematic side view of an aspect of the system including a portion of one of the gas diffusing pipes, according to an illustrative embodiment.

DETAILED DESCRIPTION

Figure 5:
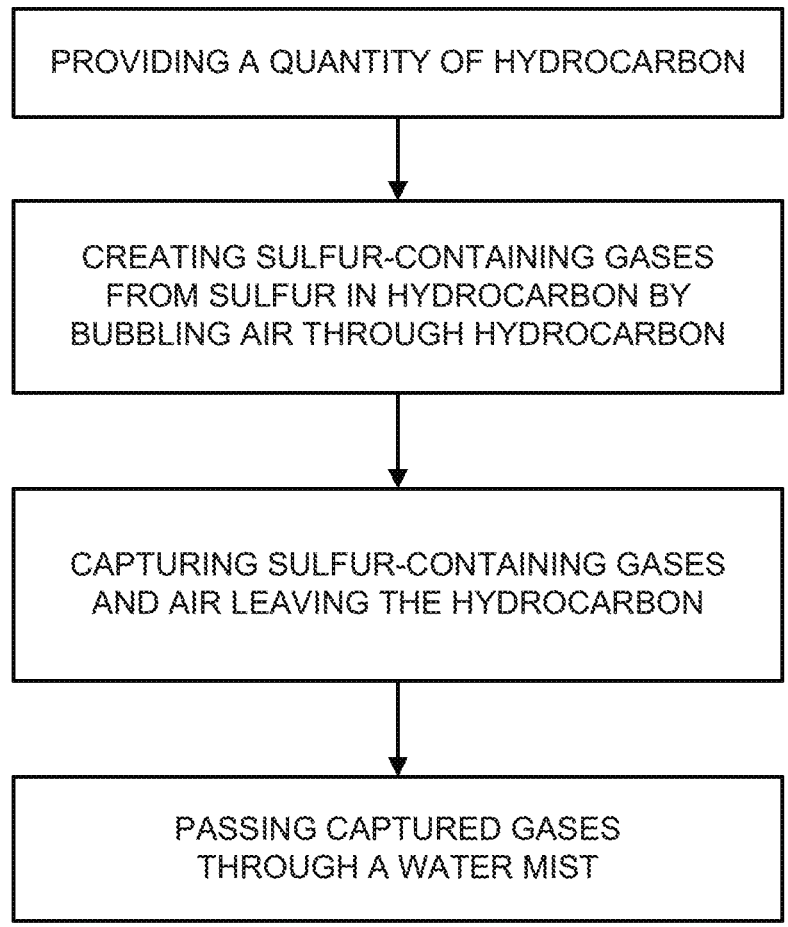
FIG. 5 is a schematic flow diagram of a method of the disclosure, according to an illustrative implementation.

With reference now to the drawings, and in particular to FIGS. 1 through 12 thereof, a new system and method for removing sulfur from hydrocarbon fluids embodying the principles and concepts of the disclosed subject matter will be described.

The presence of appreciable amounts of sulfur-containing compounds, and in particular hydrogen sulfide (H2S), in hydrocarbon liquids, such as crude oil, can have disadvantageous effects, making it desirable to remove most or all of the hydrogen sulfide content of the crude oil. Crude oil with appreciable amounts of hydrogen sulfide has been termed "sour" crude oil, while oil with lesser amounts of hydrogen sulfide is typically called "sweet" crude oil.

Various methods have been devised for the removal of sulfur-containing compounds from crude oil, such as hydrogen sulfide, in order to "sweeten" the sour oil and minimize the detrimental characteristics of relatively high sulfur content in the crude oil. However, the applicants have recognized that many of these removal techniques involve significant expense to conduct, and/or produce hazardous (and even dangerous) conditions, that make the sweetening of the crude oil not as economically or practically feasible as could be achieved.

Moreover, it is usually highly desirable to sweeten the crude oil close to the source, e.g., at the wellhead, but the wells are often located relatively remote from each other or at least from the established facilities for handling the oil. The relative remoteness of typical wells makes it highly desirable that the apparatus for removing the hydrogen sulfide is relatively portable, and does not require the frequent delivery of supplies for the system. Also, it is desirable that the system and process minimize or eliminate any production of noxious, explosive, or polluting substances as a byproduct of the removal process that are subsequently introduced into the environment.

The applicants have thus devised a system in which a flow of gas with a high content of nitrogen (N2) is passed by and through the hydrocarbon liquid to encourage the hydrogen sulfide gas dissolved in the hydrocarbon liquid to be released from the hydrocarbon liquid into the flow of nitrogen gas.

In some embodiments and implementations, the vapor pressure of the dissolved hydrogen sulfide in the hydrocarbon liquid encourages the hydrogen sulfide to redistribute between the gas flow and the liquid flow. Since the gas flow has virtually no hydrogen sulfide content, the gas flow "strips" the molecules of hydrogen sulfide from the hydrocarbon liquid, and the hydrogen sulfide is carried with the nitrogen gas flow to an element which removes a significant portion, if not substantially all, of the hydrogen sulfide from the gas flow. The nitrogen gas is not consumed by the process and may be recirculated and reused to be exposed to the flow of the hydrocarbon liquid.

In one aspect, the disclosure relates to an apparatus 10 for removing sulfur from a hydrocarbon fluid or liquid. The apparatus 10 may be used to treat batches or relatively fixed quantities of liquid, and may also be used in a continuous manner to treat a flow of the liquid.

The apparatus may include a tank 12 which holds the liquid quantity being treated. The tank 12 has an interior 14 that defines a treatment chamber 16. The tank 12 may have an upper wall 18, a lower wall 20 and a peripheral wall 22 that extends between the upper and lower walls. The upper wall 18 may have a vent opening 24 that is able to communicate with the space at the top of the chamber and the gases located there, particularly when the interior of the chamber is only partially filled with the liquid and the upper portion of the chamber is empty of the liquid and contains air as well as any gases that escape from the liquid in the tank.

In some embodiments, the apparatus 10 may also include a barrier that comprises a duct 26 that is positioned in the chamber 16 of the tank. The duct has an upper end 28 and a lower end 30, with the duct having an upper opening 32 at the upper end 28 and a lower opening 34 at the lower end. The duct is configured to permit the liquid to enter the lower opening of the duct, and in some embodiments the lower end 30 may be positioned adjacent to the lower wall 20 of the tank with a separation between the lower end of the duct and the lower wall of the tank. The duct may have a perimeter wall 36 extending between the upper end 28 and the lower end 30 of the duct. In some embodiments, the perimeter wall 36 may be flexible, and may also be collapsible, and may have a substantially circular horizontal cross section.

The apparatus 10 may also include a gas distribution manifold 40 configured to introduce or infuse a gas, such as atmospheric air, into the liquid contained in the chamber of the tank. The manifold 40 may be positioned such that it is located below the surface of the liquid in the tank chamber. In some embodiments, the manifold is positioned approximately 24 to 30 inches below the surface of the liquid, and in other embodiments the manifold is located lower in the chamber, and may be positioned adjacent to the lower wall of the tank. The manifold 40 may be mounted on the duct 26, and may be positioned toward the upper end of the duct. In some of the most preferred embodiments, the manifold 40 is located at the upper opening 32 of the duct and is positioned across the upper opening such that liquid moving through the upper opening also passes through the manifold.

In some embodiments, the gas distribution manifold 40 may include a gas distribution pipe 42 and at least one gas diffusing pipe 44, although in some of the most preferred embodiments, a plurality of gas diffusing pipes are employed. One highly effective embodiment of the manifold 40 includes a distribution pipe which extends along a closed path, and the path may be circular with a size and shape that may correspond to the size and shape if the perimeter wall 36 of the duct at the upper opening. The gas distribution pipe 42 may have an inlet 46 for receiving the gas into the manifold, which in turn may be placed into communication with a source of the gas, typically air, and the air may be supplied to the manifold at various suitable pressures. The pressure at which the gas is supplied may vary, and one factor in selecting a suitable gas pressure is the specific gravity of the liquid into which the gas is being injected. For relatively higher specific gravity liquids, relatively lower pressures may be employed such as, for example, 15 pounds per square inch (psi), and for relatively lower specific gravity liquids, relatively higher pressures may be employed, such as 150 psi. Illustratively, a range of pressures from approximately 10 psi to approximately 175 psi may be employed, and in some embodiments a range from approximately 15 psi to approximately 150 psi may be employed. In some further embodiments, a pressure of approximately 30 psi to approximately 70 psi may be employed, and in one illustrative implementation the pressure is approximately 50 psi.

The one or more gas diffusing pipes 44 may be mounted on and in fluid communication with the gas distribution pipe 42. At least a portion of the gas diffusing pipes 44 may be perforated with holes to permit gas in the interior of the diffusing pipe to exit the pipe through the perforations. In some of the more preferred embodiments, the perforations extend along a portion of the pipe 44 that is greater than half of the length of the pipe 44, and may be greater than three-quarters of the length, and in some embodiments may be substantially the entire length of the pipe 44. Each of the diffusing pipes 44 may have a proximal end 50 that is connected to the distribution pipe and a distal end 52 that is closed and is positioned relatively away from the distributing pipe 42. The gas diffusing pipes 44 may radiate from the gas distribution pipe, and may radiate inwardly from the distributing pipe. In the illustrative embodiments, the gas diffusing pipes radiate inwardly from the substantially circular distribution pipe toward a center of the manifold much the same as spokes radiate inwardly from the rim of a wagon wheel. The pipes 44 may thus be positioned across the upper opening 32 of the duct to be in communication with liquid located at and moving through the upper opening. As an example, one manifold has a gas distribution pipe with a diameter of approximately 6 feet.

The perforations or holes in the walls of the gas diffusing pipes 44 may be relatively very small to produce very small bubbles with relatively high surface area as compared to bubble of air having a larger size. It has been discovered that it is advantageous to reduce the size of the perforations or holes as the specific gravity of the liquid increases. Liquids with relatively high specific gravity may benefit from the use of holes with a measurement of approximately 0.003 inches, and liquids with relatively lower specific gravities may benefit from relatively larger holes with sizes as high as approximately 0.01.inches. In some of the most preferred embodiments of the pipes 44, the size of the perforations is approximately 0.007 inches or less. In other embodiments, the size of the perforations may be approximately 0.01 inch or less, although holes of sizes somewhat larger may be suitably used.

The apparatus 10 may further include a gas conversion structure 54 which may be in fluid communication with the vent opening 24 of the tank such that the structure 54 is in fluid communication with the upper portion of the tank chamber and the gases therein. The gas conversion structure 54 may comprise a conversion tube 56 that defines a tube interior 58 and has an inlet end 60 and an outlet end 62. The tube interior 58 may be in fluid communication with the vent opening 24 of the tank toward the inlet end 60 of the conversion tube, and may include a short pipe extending between the vent opening of the tank and the a hole in the tube to create the free flow of gases from the tank chamber to the tube interior. Preferably, the cross sectional area of the tube interior 58 at the outlet end 62 is relatively greater than the cross sectional area of the tube interior at the inlet end 60., and the decreased cross sectional area tends to cause a slight vacuum at the inlet end (and the vent opening 24 as well as the head space of the chamber in communication with the inlet end), as gas moves from the inlet end to the outlet end.

The gas conversion structure 54 may include an air injection device 64 that is configured to inject air into the tube interior 58 of the conversion tube 56 to help induce a gas flow into and through the conversion tube. The air injection device 64 may have a port 66 that is positioned in the tube interior and is in fluid communication with the tube interior toward the inlet end 60 of the conversion tube. Illustratively, the air injection device 64 may inject air into the tube interior at approximately 100 psi to approximately 150 psi, and in one illustrative implementation is at approximately 125 psi.

A water injection device 68 may be included in the gas conversion structure 54 for injecting a mist of fluid, such as water, into the tube interior 58 of the conversion tube 56 to mix the water with the gases from the tank chamber. The water injection device 68 may produce at least one stream of water droplets into the tube interior, and preferably creates a plurality of streams of droplets. In one highly preferred embodiment, the device 68 produces three streams of water droplets into the tube interior. The water injection device 68 may produce one or more streams in a downward direction into the tube interior, the water injection device being located toward the tube outlet end with respect to the port of the air injection device and the inlet end. The gas conversion structure 54 may include a fluid drain for draining away the fluid from the tube interior, which may include water and the residual sulfate.

Another aspect of the disclosure relates to a method or process for removing sulfur from a hydrocarbon liquid. The process may include providing a quantity of a hydrocarbon liquid that may contain sulfur in some form (such as sulfur-containing compounds), and this step may include placing the liquid in a tank with a space above the liquid in the chamber of the tank.

Another portion of the process may include creating sulfur-containing gasses from the sulfur and sulfur-containing compounds in the hydrocarbon liquid. This may include injecting air into the hydrocarbon liquid to create sulfur-containing gases such as hydrogen sulfide, and injecting the air may be performed by creating a plurality of air bubbles in the liquid. A highly suitable manner of performing this act is through the positioning of the gas distribution manifold in the liquid and moving air through the manifold and out through the perforations. The air may be pressurized to force the air into the liquid through the holes.

In some implementations, the manifold may be positioned adjacent to the upper opening of a duct such as is described herein. In such implementations, the infusion of the air may tend to induce movement in the fluid, with the fluid being induced to move out of the upper opening of the duct, thus tending to pull fluid into the lower opening of the duct, and in turn pulling fluid from the tank located outside the duct (but into the chamber) downwardly toward the lower opening. In other implementations, the manifold may be utilized in a tank without the duct, and may be positioned below the liquid surface such as adjacent to the lower wall of the tank. Such an implementation may be more suitable for use in relatively smaller tanks and quantities of the liquid.

Another portion of the process includes capturing gases from a space above the hydrocarbon liquid, including the air being infused into the tank and the hydrogen-containing gases created, such as the hydrogen sulfide generated. The capture may be effected by inducing a flow of the gases from the space above the liquid and into a structure such as the gas conversion structure described herein.

The captured gases may be passed through a mist of water droplets, and the captured gases may be passed through the gas conversion structure. A flow of the captured gases may be induced through the structure, and may be accomplished by injecting air into the structure to create a flow of air through the structure and inducing gas flow from the tank and into the structure. The process may also include providing the structure with an increasing cross sectional area to induce a vacuum in the flow of air and captured gases passing through the structure. A mist of water may be created in the flow of air and captured gases, and droplets of water may be sprayed from one or more nozzles into the flow of air and gases. Residual water and sulfur compounds in the water may be removed from the structure.

Figure 6:
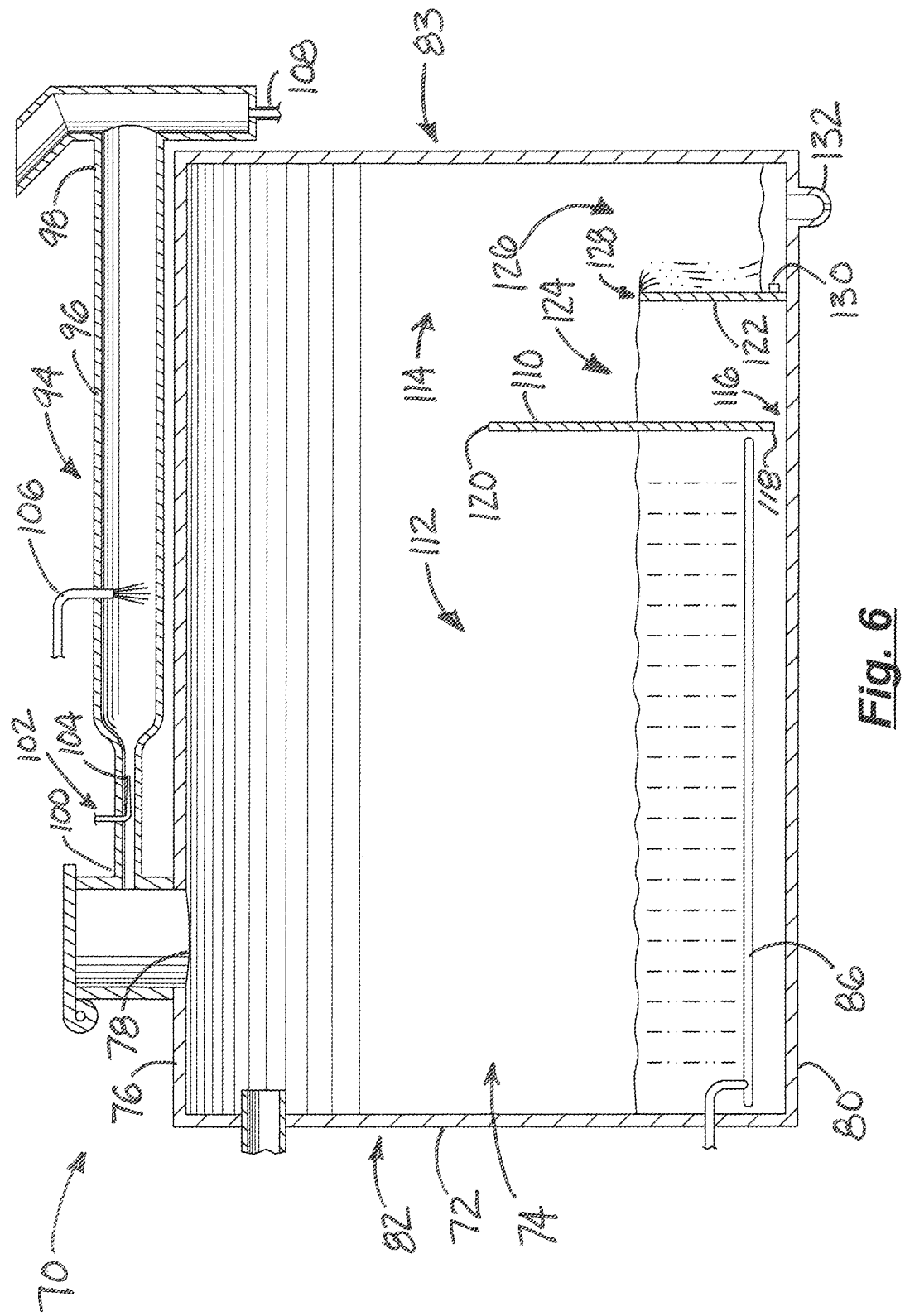
FIG. 6 is a schematic sectional view of the apparatus according to other embodiments of the disclosure, with the section being taken along a vertical plane.
Figure 7:
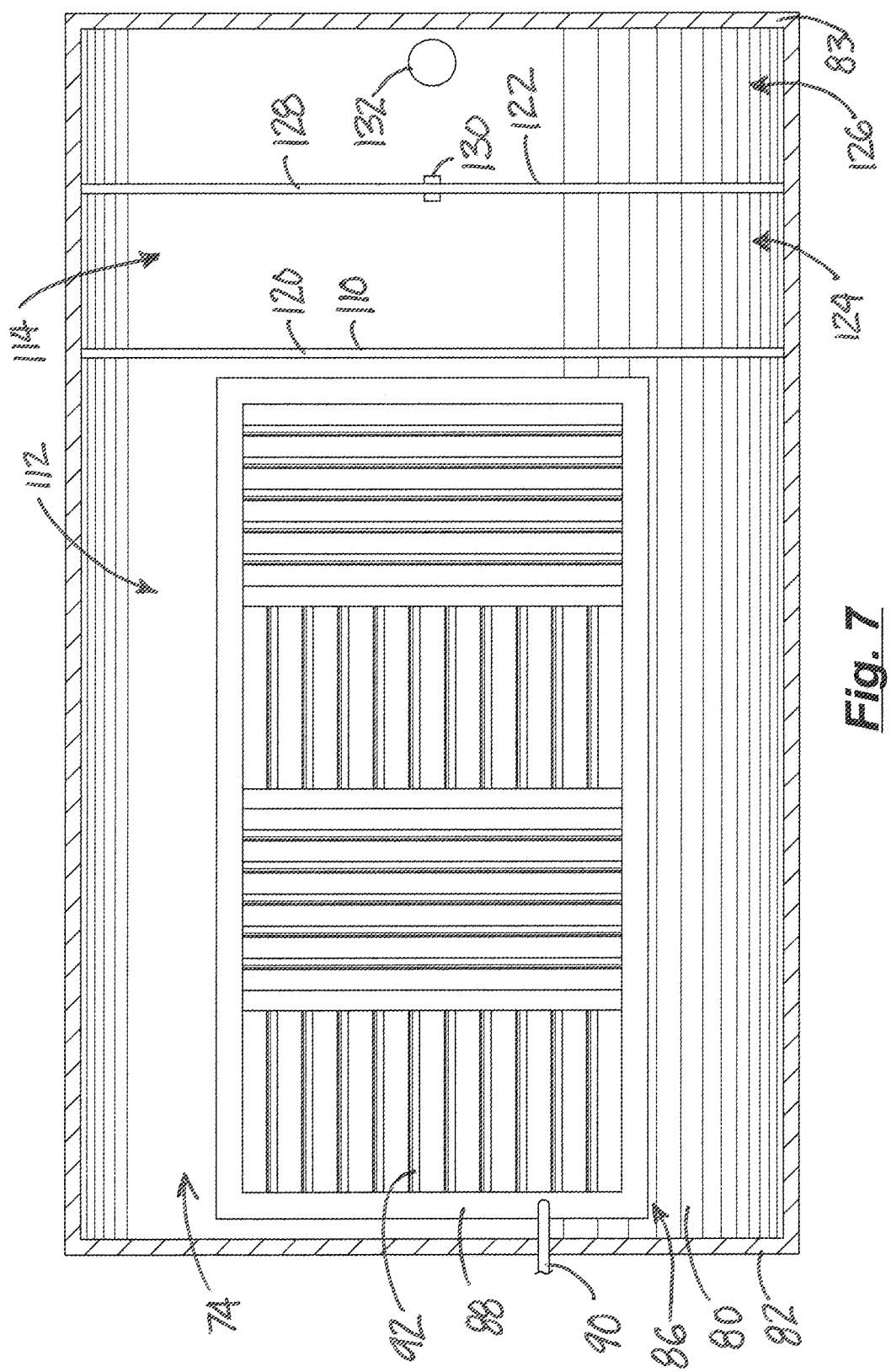
FIG. 7 is a schematic sectional view of an apparatus with a configuration generally corresponding to the embodiments shown in FIG. 6, with the section being taken along a horizontal plane.
Figure 8:
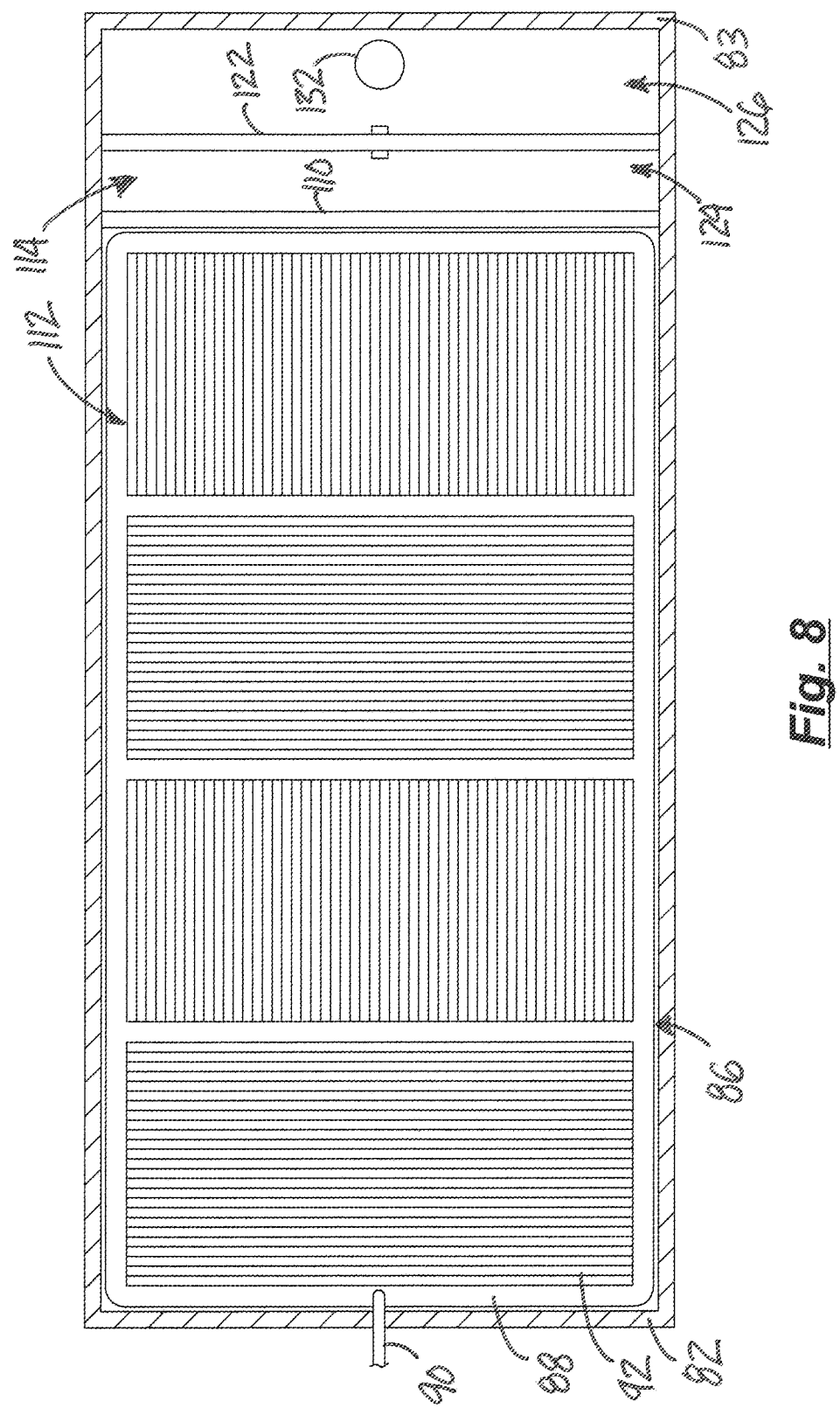
FIG. 8 is a schematic sectional view of an apparatus with another configuration generally corresponding to the embodiments shown in FIG. 6, with the section being taken along a horizontal plane.
Figure 9:
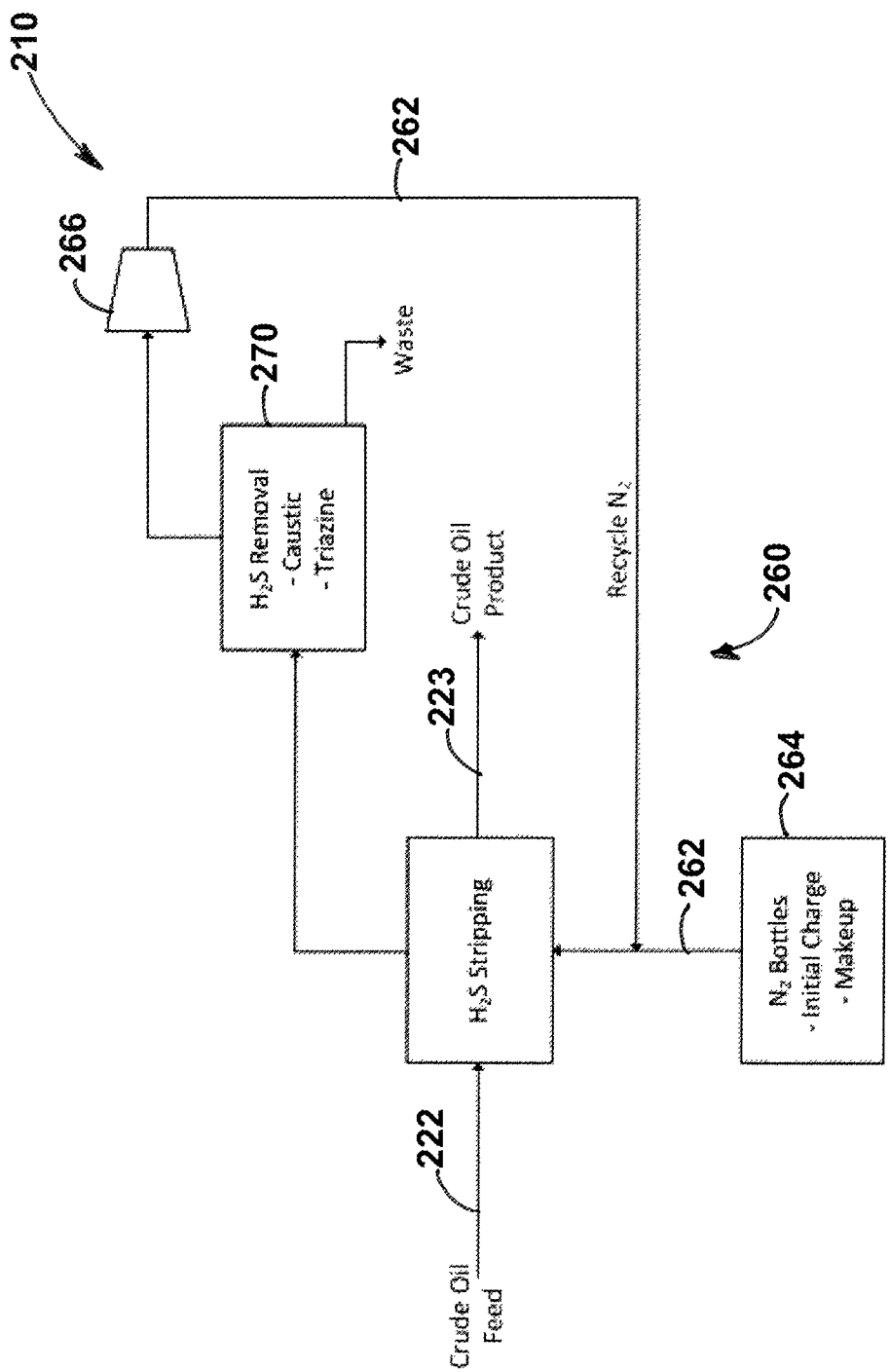
FIG. 9 is a schematic diagram of another embodiment of the system for sulfur or sulfur-compound removal from hydrocarbon liquids according to the present disclosure.

Other embodiments of the apparatus may include many similar but not identical aspects of the embodiments disclosed above. As shown in FIGS. 6 through 8, the embodiments of the apparatus 70 are also capable of removing contaminants, such as sulfur, from a liquid such as a hydrocarbon liquid, and may be more suitable for performing removal in a continuous manner (e.g., from a continuous or substantially continuous flow of the liquid). The embodiments also include a tank 72 which has an interior defining a chamber 74 and which has an upper wall 76 and an opening 78. The opening may be designed as a manway to provide access to the chamber of the tank when needed, although this configuration is not critical. The tank 72 may also have a lower wall 80, In some embodiments, the tank 73 is elongated in a horizontal direction, rather than in the vertical direction. The elongated shape tank 72 may have a first end 82 and a second end 83, and the first end may be an inlet end and the second end may be an outlet end. The tank may have a substantially cylindrical shape, with the cylindrical shape being elongated along a horizontal axis and the tank may have an elongated substantially cubical or three dimensional rectangular shape which may be elongated in the horizontal direction.

The apparatus 70 may also include a gas distribution manifold 86 for introducing the gas into the liquid in the tank. The gas distribution manifold 86 may be mounted or positioned in the interior of the tank for submergence in the liquid when liquid is positioned in the tank chamber 74. The manifold 86 may be located relatively low in the chamber of the tank, such as close to the lower wall. In some of the most preferred embodiments, the manifold 86 extends in a generally horizontal plane, but may be slanted to some degree, or have portions that are substantially horizontal and portions that are not horizontal. The manifold 86 may extend from one side wall of the tank to another side wall, although this is not critical, although maximizing the amount of air moved into the liquid through the manifold may make the processing of the liquid faster and more complete, so maximizing the size of the manifold (and thus the number of perforations in the manifold) for the size of tank may be advantageous.

The manifold 86 may include a gas distribution pipe 88, and the pipe 88 may extend along a closed path with an inlet 90 for receiving the gas. The gas distributing pipe 88 may extend along a substantially rectangular path, although the shape of the path is not critical to the operation of the apparatus. It is desirable to have the manifold 86, and any distribution pipe 88 that forms the perimeter of the manifold, to extend across the chamber as far as practicable. For example, as shown in FIG. 8 showing the cross section of a tank having a substantially rectangular cross sectional shape in a vertical plane, the manifold extends to the long side walls while as shown in FIG. 7 showing the cross section of a tank having a substantially circular cross sectional shape in vertical plane, the manifold extends a more limited distance horizontally toward the sides due to the wall of the tank gradually sloping upward from the lower most point.

The gas distribution manifold 86 may also include at least one gas diffusing pipe 92 mounted on and in fluid communication with the gas distribution pipe 88, with at least a portion of the gas diffusing pipe being perforated with holes to permit gas in the interior of the diffusing pipe to exit the pipe. The diffusing pipe 92 may have one or both ends fixed to and in communication with the distribution pipe 88. A plurality of the gas diffusing pipes 92 may be connected to the distribution pipe, and groups of the diffusing pipes may be oriented in different directions, such as in perpendicular directions.

The apparatus 70 may also include a gas conversion structure 94 in fluid communication with the interior of the tank 72 via the opening 78 of the tank. The gas conversion structure may comprise a conversion tube 96 defining a tube interior in fluid communication with the opening 78 of the tank. The conversion tube may have a cross sectional area at an outlet end 98 that is relatively greater than a cross sectional area 100 of the interior at the inlet end. The gas conversion structure may also include an air injection device 102 that is configured to inject air into the interior of the conversion tube, and may have a port 104 in fluid communication with the inlet end of the conversion tube. The gas conversion structure may also include a water injection device 108 that is configured to inject a mist of water into the interior of the injection tube, and may produce at least one stream of water droplets into the tube interior. The gas conversion structure may also include a fluid drain 108 configured to drain water and sulfate as well as other substances precipitated out of the gases exiting the chamber.

The apparatus 70 may also utilize a first interior wall 110 as a barrier positioned in the interior of the tank 72 and which may extend across a portion of the chamber of the tank. The first interior wall 110 may divide the chamber 74 into a first chamber portion 112 and a second chamber portion 114, although the division may not be a complete isolation of the portions 112, 114 from each other. The first chamber portion 112 may be located toward the inlet end 82 of the tank, and the second chamber portion may be located toward the outlet end 83 of the tank. The first interior wall 110 may extend upwardly from the lower wall 80 toward the upper wall 76. A gap 116 may be located between a portion of the first interior wall 110 and the lower wall 80, and the first interior wall may have a lower edge 118 that is spaced from the lower wall 80 to form the gap 116. The first interior wall 110 may have an upper edge 120 that is spaced from the upper wall 76. In some embodiments, the first interior wall 110 may extend approximately 40% to approximately 60% of a distance between the lower wall 80 and the upper wall 76, and in some embodiments the first interior wall 110 may extend approximately half of a distance between the upper wall and the lower wall. The first interior wall may be positioned a distance from the inlet end of the tank that is about 50 percent to 80 percent of the total length of the chamber, so that the first chamber portion is greater in length (and corresponding volume size) than the second chamber portion.

The apparatus 70 may also include a second interior wall 122 in the interior of the tank 72 and which may extend across a portion of the chamber 74 of the tank. The second interior wall 122 may divide the second chamber portion 114 into a first subchamber 124 and a second subchamber 126, although the division between the subchambers may not create a complete separation. The first subchamber 124 may be in fluid communication with the first chamber portion 112 through the gap 116. The second interior wall 122 may extend upwardly from the lower wall 80 toward the upper wall 76 of the tank. The first subchamber 124 may be positioned between the second interior wall 122 and the first interior wall 110. The second subchamber may be located between the second interior wall and the second (outlet) end 83 of the tank. The height of a top edge 128 of the second interior wall above the lower wall may be less than the height of the top of the first interior wall above the lower wall 80, and the height of the second interior wall may be less than half of the height of the first interior wall. A closable drain hole 130 may be formed in the second interior wall toward a bottom of the second interior wall for draining fluid from the bottom of the tank.

A sump 132 may be formed in the lower wall 80 of the tank for draining the liquid from the tank, including liquid that has passed over the second interior wall into the second subchamber.

The gas distribution manifold 86 may be positioned at a height from the lower wall that is less than the height of the upper edge 120 of the first interior wall, and as a result below the surface of the liquid in the chamber of the tank. In some embodiments, the position of the gas distribution manifold with respect to the upper surface of the lower wall may be that the manifold rests upon the upper surface of the lower wall, although some separation between the manifold and the lower wall is often desirable so that the manifold does not rest in any accumulation of solids one the upper surface of the lower wall. In some embodiments, the manifold may be up to approximately 12 inches from the lower wall upper surface, and may be approximately 3 inches to approximately 12 inches from the lower wall, and may be approximately 3 inches to 8 inches from the lower wall upper surface.

In an illustrative embodiment, the tank has a chamber with a height of approximately 8 feet, a width of approximately 8 feet, and a length of approximately 16 feet. The first interior wall may be approximately 12 feet from the inlet end. The first interior wall may have a height measured from the lower wall of approximately 4 feet, and the gap formed beneath the first interior wall may be approximately 2 inches. The height of the second interior wall may be approximately 18 inches. The second interior wall may be located approximately 14 feet from the inlet wall.

Liquid that enters the chamber 74 of the tank moves into the first chamber portion 112 and is exposed to the gas bubbles escaping from the perforations from the gas diffusing pipes 92 of the gas distribution manifold. The liquid may move through the gap 116 into the first subchamber and fill the first subchamber to the top edge 128 of the second interior wall. As the liquid fills the first chamber portion and then fills the first subchamber of the second chamber portion, the liquid moves over the second interior wall into the second subchamber. As the liquid moves over the top edge of the second interior wall, any gas bubbles that remain entrained in the liquid are caused to move out of the liquid as the thin flow of liquid passes over the wall. As the liquid moves into the second subchamber it drains from the tank chamber through the sump 132.

In most of the preferred embodiments, utilizing atmospheric or environmental air as the gas moving through the liquid has benefits of ready availability, although it is conceivable that other gases may be utilized. It has been recognized by the applicants that air that is heated to a temperature that is higher than the temperature of atmospheric air may be more suitable for processing some wastes, and air at temperatures up to approximately 100 degrees F. to approximately 150 degrees F. or more may be utilized, typically by heating air drawn from the atmosphere before introducing the air into the gas distribution manifold.

In another aspect, the disclosure relates to a system 210 and method for removing sulfur and sulfur-containing compounds, in particular hydrogen sulfide (H2S) from a liquid, typically a hydrocarbon liquid such as crude oil which has been removed from a well but has received minimal, if any, treatment or processing prior to being utilized in the system. The system and method is particularly useful for treating so-called "sour" crude which include an appreciable amount of hydrogen sulfide.

Figure 10:
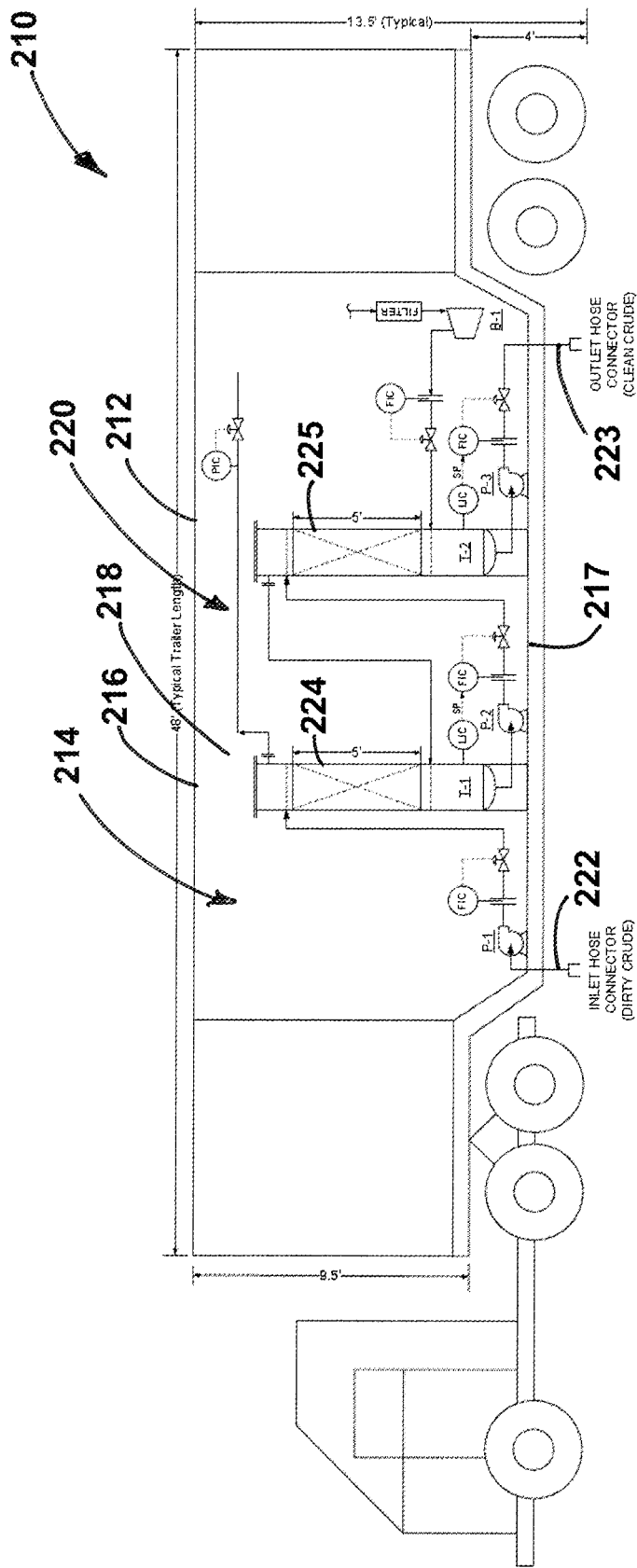
FIG. 10 is a schematic side view of an illustrative embodiment of the system including a transportable enclosing container, according to an illustrative embodiment.
Figure 11:
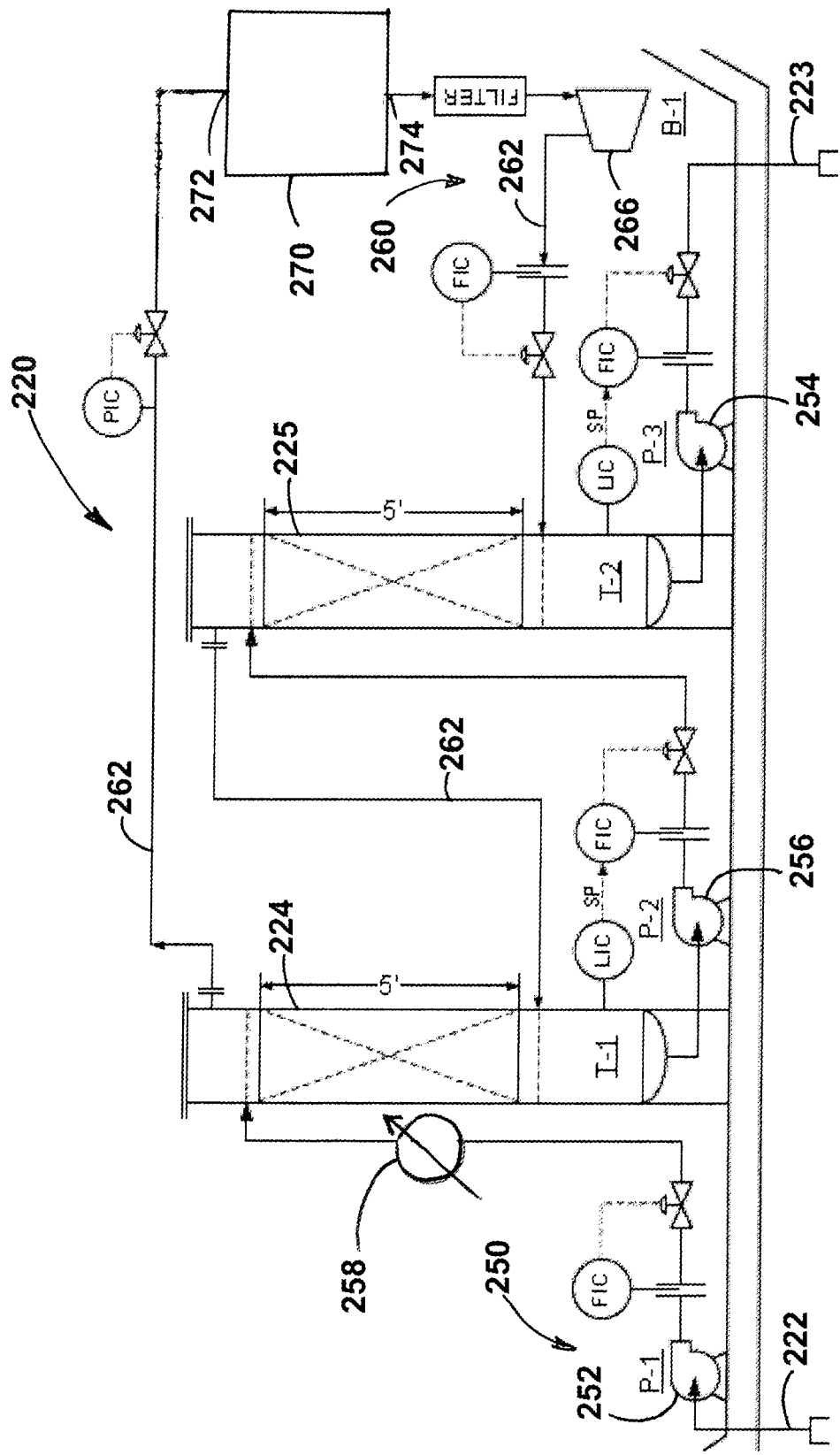
FIG. 11 is a schematic side view enlarged to show elements of the system, according to an illustrative embodiment.
Figure 12:
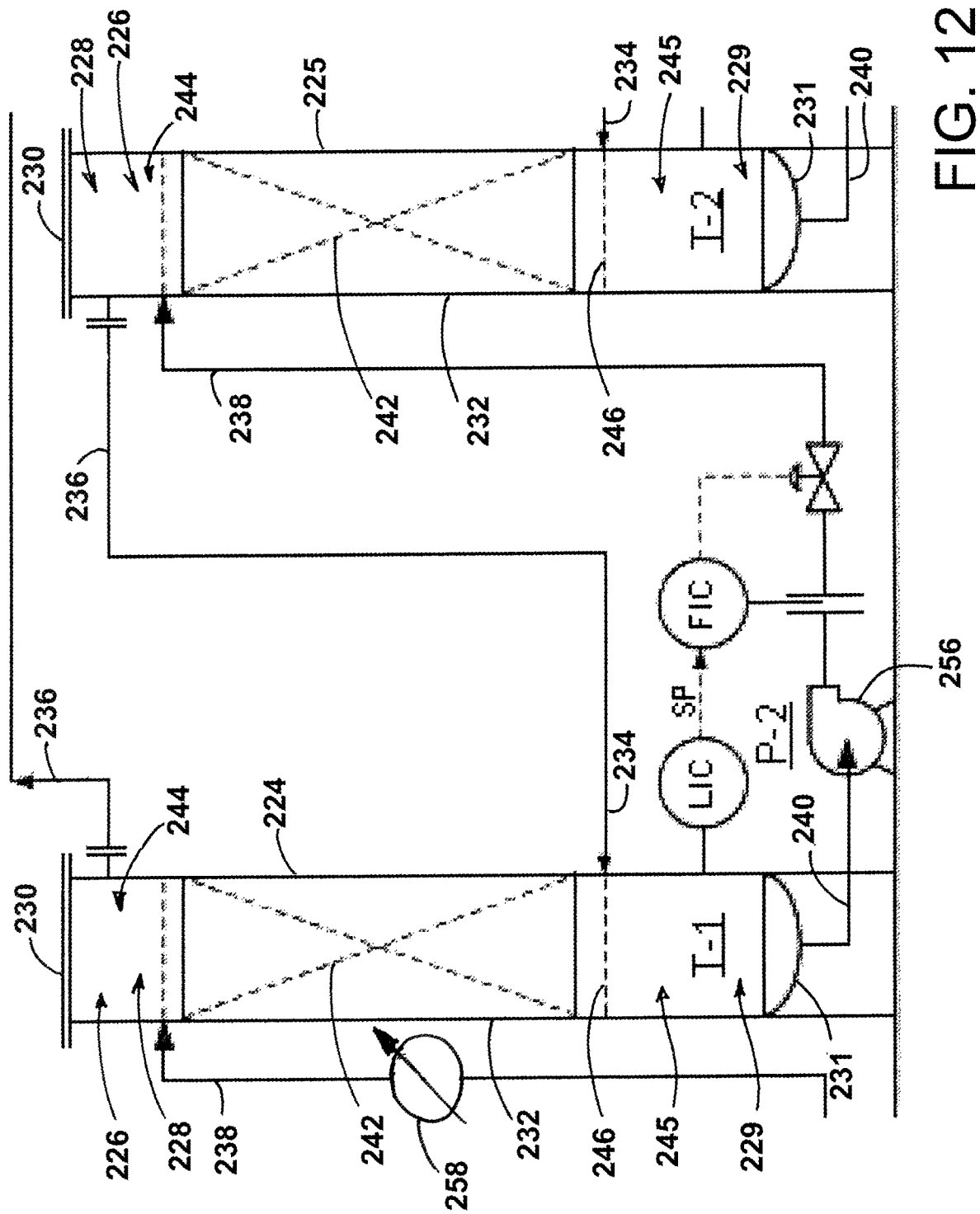
FIG. 12 is a schematic side view further enlarged to show elements of the system, according to an illustrative embodiment.

The system 210 may include a container 212 for containing various elements of the system in a manner enhancing the portability of the system for movement to locations adjacent to wellheads and treating the crude oil proximate to the well from which it was drawn. An illustrative container 212 may define an interior 214 in which elements of the system are contained such that the system may be substantially self-contained within the interior of the container. An illustrative container 212 may have a top wall 216, a bottom wall 217, and the plurality of side walls 218 that extend between the top 216 and bottom 217 walls to substantially enclose the interior 214 and the elements of the system within the interior. In some embodiments, the container 212 may comprise a portion or the entirety of a trailer, such as a semi-trailer towable by a semi-tractor over the road for movement between remote locations (such as illustrated in FIG. 10). In other embodiments, the container 212 may comprise a shipping container of the type typically utilized for transporting goods and often having a standard and uniform size and shape to facilitate transport over the road, over the rail, and by ship. Other types of in forms of containers may also be utilized.

The system 210 may also include an apparatus 220 for removing sulfur-containing compounds, and more specifically hydrogen sulfide, from a hydrocarbon fluid which is typically in the form of a hydrocarbon liquid and usually comprises crude oil. The hydrocarbon liquid may be understood as comprising crude oil drawn from an oil well which may have a content of hydrogen sulfide at a level that is desirable to be reduced. Typically the hydrogen sulfide is in a gaseous state which is dissolved in the liquid crude oil. The apparatus 220 of the disclosure is highly suitable for removing sulfur, or sulfur-containing compounds, particularly hydrogen sulfide, from a stream of a hydrocarbon liquid, although aspects of the disclosure may be applied to batches or fixed quantities of a hydrocarbon liquid processed at one time.

The apparatus 220 may be substantially contained or enclosed within the interior 214 of the container 212, which may advantageously facilitate the movement of the apparatus 220 between locations, and in particular to remote locations, although it should be recognized that the apparatus 220 may be utilized without the container 212 and may be relatively stationary.

In some greater detail, the apparatus 220 may have a fluid input 222 configured to receive hydrocarbon liquid, such as untreated crude oil withdrawn from an oil well. The apparatus 220 may also have a fluid output 223 configured to dispense treated hydrocarbon liquid with a reduced hydrogen sulfide content in comparison to the hydrocarbon liquid at the fluid input.

The apparatus 220 may include at least one tank 224, and may suitably include multiple tanks 224, 225 which may have similar configurations to each other. In apparatus having multiple tanks, the tanks may be connected and operated in series with respect to each other to enhance the overall effectiveness of hydrogen sulfide removal by the apparatus, or the tanks may be connected in parallel with respect to each other to enhance the overall flow rate of the hydrocarbon liquid through the apparatus. Optionally, combinations of series and parallel arrangements of pluralities of the tanks may be utilized to achieve desired removal effectiveness and removal flow rates through the apparatus. For the purposes of this description, a pair of similar tanks connected in series will be described with the understanding that the attribution of a feature to one tank may be understood to also be a feature of the other tank (or tanks) as well.

The tank 224 may define a chamber 226 therein which has a top end 228 and a bottom end 229, and may be elongated in a substantially vertical direction between the top 228 and bottom 229 ends. The tank may include an upper wall 230 and a lower wall 231, as well as a perimeter wall 232 which extends between the upper 230 and lower 231 walls. The perimeter wall 232 may be joined to the lower wall 231 in a manner that is configured to hold a liquid, and the perimeter wall may be joined to the upper wall in a manner configured to confine a gas. The tank may be closed except for certain specific inlets and outlets. Illustratively, the tank may have a gas inlet 234 through which a gas flow may be introduced into the chamber 226, and a gas outlet 236 through which a gas flow may exit the chamber. The gas outlet 236 may be vertically spaced from the gas inlet 234 such that the gas outlet is located at a higher vertical level than the gas inlet on the tank. The gas inlet 234 may be located toward the bottom end 229 of the chamber and the gas outlet 236 may be located toward the top end 228 of the chamber. The gas inlet and the gas outlet may be located on the perimeter wall, although placement of the gas inlet and outlet on other elements of the tank may be utilized.

The tank 224 may include a fluid inlet 238 through which the hydrocarbon liquid is introduced into the chamber 226, and may also have a fluid outlet 240 through which the hydrocarbon liquid may exit the chamber. The fluid inlet 238 may be vertically spaced from the fluid outlet 240 such that the fluid inlet is located at a higher vertical level than the fluid outlet. The fluid inlet 238 may be located toward the top end 28 of the chamber and the fluid outlet 240 may be located toward the bottom end 229 of the chamber. In some embodiments, the gas outlet 236 may be located at a vertical level that is higher on the tank then the fluid inlet 238, and the fluid outlet 240 may be located at a vertical level that is lower on the tank than the gas inlet 234.

The gas inlet 234 and gas outlet 236 as well as the fluid inlet 238 and fluid outlet 240 may be positioned on the tank in a manner that causes movement or flow of the hydrocarbon liquid in the tank chamber 226 in a generally downward direction from fluid inlet to fluid outlet, and the movement or flow of the gas in a generally upward direction from the gas inlet to the gas outlet. These relatively opposite directions of movement may create a contraflow or counterflow (e.g., flows in opposite, or substantially opposite, directions) of the gas and the liquid as the gas and the liquid move from the respective inlets to the respective outlets on the tank. The counterflow may result from the gas inlet 234 and gas outlet 236 being arranged on the tank 224 to create a flow in the tank chamber between the gas inlet and gas outlet that is opposite or substantially opposite in direction to a flow of the fluid from the fluid inlet and the fluid outlet in the tank chamber. Since the flows occur in the same (or substantially the same) space or portion of the chamber, a crossflow of the liquid and the gas may also be created. Crossflow may be further enhanced by the gas inlet 234 and gas outlet 226 being located in some embodiments on substantially opposite sides of the perimeter wall 232 of the tank. The counterflow and/or cross flow of the flows enhance the opportunity for the gas an fluid to interface and interact.

In embodiments including multiple tanks connected in series, the fluid outlet of the first tank 224 may be in fluid communication with the fluid inlet of the second tank 225 such that fluid exiting the chamber of the first tank enters the chamber of the second tank as fluid flows between the fluid input 222 and the fluid output 223 of the apparatus 220. Also, the gas outlet of the second tank 225 may be in fluid communication with the gas inlet of the first tank 224 such that gas exiting the chamber of the second tank enters the chamber of the first tank.

The tank may include a contacting section 242 which is positioned in the chamber of the tank and which may form a partial barrier to liquid flow in the chamber as well as a partial barrier to gas flow in the chamber, while not forming a complete barrier which prevents flow of either the liquid or the gas. The contacting section may be configured to facilitate or enhance the intermixing of and contact between the descending liquid moving between the fluid inlet and fluid outlet and the rising gas moving between the gas inlet and gas outlet. The contacting section 242 may be positioned between the gas inlet and the fluid outlet located toward the bottom end of the chamber and the gas outlet and the fluid inlet located toward the top end of the chamber. At least a portion of the contacting section 242 may extend substantially vertically in the chamber. An upper gap 244 may be defined between the upper wall 230 of the tank and an upper portion or limit of the contacting section 242, and a lower gap 245 may be formed between the bottom wall 231 and a lower portion or limit of the contacting section. In some embodiments, the contacting section 242 may comprise, for example, one or more packed beds, to promote intimate contact between the gas and the liquid. The type of packing can be "structured packing" or "random packing" as understood in the art. As another example, the contacting section may comprise a plurality of baffles or trays which may incompletely extend across the chamber in a direction substantially perpendicular to the general vertical direction of flow of the liquid and the gas in the tank chamber. Illustratively, one or more of the trays may catch liquid moving downwardly, the liquid may flow across the trays, and then the liquid may flow downwardly through a "downcorner" and onto the next (lower) tray, and so forth, while the gas flows upwardly through holes in the trays. The holes in the trays may be equipped with bubble caps or valves to enhance the contacting surface area. Other suitable structures for enhancing contact between the gas flow and liquid flow may also be used in the contacting section.

The tank may also include a gas distribution manifold 246 for introducing the gas into the interior of the tank. The gas distribution manifold 246 may be located toward the bottom end 229 of the chamber. The gas distribution manifold 246 may comprise one or more tubes or pipes and at least a portion of the tubes of the gas distribution manifold 246 may be perforated with holes to permit gas in the interior of the tubes of the manifold 246 to exit the manifold. The interior of the gas distribution manifold may be in communication with the gas inlet 234 of the tank to thereby receive the gas moving into the chamber. The gas distribution manifold may be positioned below the contacting section 242 in the chamber at approximately the vertical height of the gas inlet.

The apparatus 220 may also include a fluid circulation assembly 254 configured to circulate the hydrocarbon fluid along a fluid path defined between the fluid input 222 and fluid output 223 of the apparatus. The fluid circulation assembly 250 may include an input pump 252 which may be in fluid communication with the fluid input 222 of the apparatus and the fluid inlet 238 of the tank, which is the first tank in apparatus having multiple tanks. Suitable piping may connect the fluid inlet of the apparatus to the input pump 252 and the input pump to the fluid inlet of the tank. The fluid circulation assembly 250 may also include an output pump 254 which may be in fluid communication with the fluid output 223 of the apparatus and the fluid outlet 240 of the tank. In those embodiments employing two tanks, the output pump may be connected to the fluid outlet of the second tank. Suitable piping may connect the fluid output of the apparatus to the output pump 254 and the output pump to the fluid outlet of the tank.

In embodiments employing multiple tanks, an intermediate pump or pumps 256 may be employed in the fluid path between the tanks to facilitate fluid movement between the tanks, drawing liquid from the bottom end of the chamber of one tank and moving the liquid to the top end of another tank. Illustratively the intermediate pump 256 may be in fluid communication with the fluid output of the first tank and the fluid input of the second tank to thereby transfer or move the liquid from the first tank to the second tank.

In some embodiments, the apparatus 220 may include means for heating the hydrocarbon fluid for the purpose of reducing the viscosity of the hydrocarbon fluid to thereby facilitate the flow of the fluid through the contacting section, such as the packed beds, and further enhance the stripping of the sulfur compounds from the fluid. The hydrocarbon fluid may thus be heated before the fluid is brought into contact with the gas flow, such as before the fluid is introduced into the fluid inlet 238 of the tank. Illustratively, a fluid heater 258 of a type suitable for heating hydrocarbon fluid may be positioned along or prior to the fluid inlet 238 of the tank. The benefits provided by heating the fluid prior to entering the contacting section may depend upon, in part, the nature of the hydrocarbon fluid and the ambient temperature (and thus the temperature of fluid entering the apparatus 220).

The apparatus 220 may also include a gas circulation assembly 260 which is in communication with the tank and may be configured to induce and cause a gas flow through the chamber of the tank. The gas circulation assembly 260 may include a gas conduit 262 which may define a portion of the gas path for gas flow between the gas outlet 236 of the tank and the gas inlet 234 of the tank to create a substantially continuous gas path or circuit through elements described herein. The gas conduit 262 may be fluidly connected to the gas inlet 234 of the tank, and may also be fluidly connected to the gas outlet 236 of the tank. In multiple tank configurations, the gas conduit 262 may extend between the gas outlet 236 of the first tank 224 and the gas inlet 234 of the second tank 225, as well as the gas outlet of the second tank 225 and the gas inlet of the first tank 224 to create a circuit with the tanks and other elements of the apparatus described herein.

The gas circulation assembly 260 may also include a gas source 264 which may contain a quantity of gas to be circulated through the gas conduit 262 and other elements of the apparatus, including the tanks. Significantly, the gas provided from the gas source 264, and circulated through the apparatus 220, includes nitrogen (N2) gas, and is predominately nitrogen gas. In some implementations, the gas of the gas flow from the gas source has a content of at least 90% nitrogen gas (N2) by volume, and in some implementations the gas has at least 95 percent nitrogen gas (N2) by volume. In some other implementations, the gas has at least 98 percent nitrogen gas (N2) by volume, and in still other implementations the gas has a content of approximately 100 percent nitrogen gas (N2) by volume. In some of the most highly preferred implementations, a gas flow with greater than approximately 98 percent nitrogen gas (N2) by volume is utilized. It will be recognized that the highest nitrogen gas (N2) content in the gas flow occurs before the gas flows into the tank or tanks and is exposed to the hydrocarbon liquid, where other gaseous substances (including hydrogen sulfide) are picked up by and then included in the gas flow. The presence of other gases in the gas flow, and in particular oxygen, increases the potential for creating explosive gases and therefore gases flows having over approximately 5 percent to approximately 10 percent by volume of gases other than nitrogen gas are not preferred.

The gas circulation assembly 260 may also include a gas compressor 266 which is configured to circulate the gas flow along the gas path including moving the gas flow through the various elements of the apparatus 220 such as the tanks, conduits, etc. The gas compressor may be in fluid communication with the gas inlet of at least one of the tanks, and may also be in communication with the gas outlet of at least one of the tanks. The relatively higher pressure at the gas inlet 234 of the tank, and relatively lower pressure at the gas outlet 236 of the tank, produced by the operation of the compressor 266 may cause the movement of the gas flow in the tank between the inlet 234 and outlet 236.

The apparatus 220 may also include a gas processor assembly 270 configured to remove hydrogen sulfide (H2S) from the gas flow moving along the gas path, such as the gas flow that has passed through the tank or tanks and may thus include hydrogen sulfide stripped from the hydrocarbon liquid. The gas processor assembly 270 may include a sour gas input 272 which may be in fluid communication with the gas outlet 236 of one of the tanks, and a sweetened gas output 274 which may be in fluid communication with the gas inlet 234 of one of the tanks (via the gas compressor).

The gas processor assembly 270 may include any suitable apparatus and process for removing the hydrogen sulfide from the gas flow. In some implementations, the hydrogen sulfide in the gas flow may be exposed to gas treatment chemical compounds, sometimes referred to as scavengers.

For example, the gas flow with the acidic hydrogen sulfide may be exposed to the basic sodium hydroxide to form sodium sulfide, a salt:

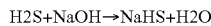

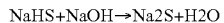

In another example, the gas flow may be exposed to triazine to form dithiazines through a series of reactions. The products of the reactions may remain in a carrier solvent (such as a mixture of methanol and water) which may then be disposed of in a suitable manner. Any gaseous hydrocarbons carried in the gas flow may thus be directed back along the gas path to the tanks.

In other implementations, the gas flow may be exposed to a solid chemical compound, such as a metal oxide, which may react with the sulfur compounds in the gas flow to form solid metal sulfides to thus remove the sulfur compounds from the gas flow. The solid metal compounds may then be disposed of in a suitable manner.

The gas processor assembly 270 may be connected to the gas compressor 262 so that, after the gas flow has passed through the gas processor assembly and the hydrogen sulfide has been removed from the gas of the gas flow, the gas flow may be passed through the gas compressor 266 to be reintroduced into the tank or tanks through a gas inlet 234. The gas flow, and in particular the nitrogen (N2) gas of the gas flow, is thus recycled for use by the apparatus 220. Additional nitrogen gas may be added to the gas flow from the gas source 264 as needed to make up for losses in the volume of gas in the gas flow. Losses of the nitrogen gas may occur, for example, through nitrogen gas becoming dissolved in the hydrocarbon liquid and through any leaks in the apparatus 220.

In operation, the apparatus 220, and in particular the tank or tanks and the elements of the gas circulation assembly 260, may be charged or filled with a gas that includes the nitrogen gas by drawing the nitrogen gas from the gas source 264. Circulation of the gas flow along the gas path may be produced by operation of the gas compressor 266 as well as the opening of any valves along the gas path. Once a suitable level of gas circulation has been established through the gas path of the apparatus 220, a flow of the hydrocarbon liquid or crude oil may be initiated through the apparatus via the fluid input 222.

The hydrocarbon liquid may pass through an input pump 252 (and a fluid heater 258) and move into the chamber 226 of the first tank 224 through the fluid inlet 238 of the tank 224. The hydrocarbon liquid moves downwardly under the influence of gravity through the chamber 226 of the first tank and through the partial barrier of the contacting section 242 positioned in the chamber. Simultaneously, gas flow along the gas path moves in an upward direction in the chamber 226 of the first tank 224 and through the contacting section 242 in a substantially opposite direction to the overall downward movement direction of the hydrocarbon liquid. The hydrocarbon liquid collecting at the bottom end 229 of the chamber is moved through the fluid outlet 240 (such as by operation of the intermediate pump 256) and directed through the fluid inlet 238 and into the chamber 226 of the second tank 225, while gas flow leaving the chamber of the first tank 224 moves along the gas path to the gas processor assembly 270.

In the second tank 225, downward movement of the hydrocarbon liquid is again met by upward movement of the gas flow on the gas path through the contacting section 242. Hydrocarbon liquid collecting in the bottom end 229 of the second tank chamber is drawn through the fluid outlet 240 by output pump 254 which moves the liquid to the fluid output 223 of the apparatus as the processing of the hydrocarbon liquid has been completed. Gas flow from the second tank 225 exits the chamber through the gas outlet 236 and moves to the gas inlet 234 of the first tank 224.

In this process, the fluid flow and the gas flow are not only conducted in opposite directions within the chambers of the respective tanks, but also in opposite directions among the multiple tanks. More specifically, gas flow is initially moved through the second tank before moving through the first tank, while fluid flow is moved through the first tank before moving through the second tank.

It should be appreciated that in the foregoing description and appended claims, that the terms "substantially" and "approximately," when used to modify another term, mean "for the most part" or "being largely but not wholly or completely that which is specified" by the modified term.

It should also be appreciated from the foregoing description that, except when mutually exclusive, the features of the various embodiments described herein may be combined with features of other embodiments as desired while remaining within the intended scope of the disclosure.

Further, those skilled in the art will appreciate that the steps shown in the drawing figures may be altered in a variety of ways. For example, the order of the steps may be rearranged, substeps may be performed in parallel, shown steps may be omitted, or other steps may be included, etc.

With respect to the above description then, it is to be realized that the optimum dimensional relationships for the parts of the disclosed embodiments and implementations, to include variations in size, materials, shape, form, function and manner of operation, assembly and use, are deemed readily apparent and obvious to one skilled in the art in light of the foregoing disclosure, and all equivalent relationships to those illustrated in the drawings and described in the specification are intended to be encompassed by the present disclosure.

Therefore, the foregoing is considered as illustrative only of the principles of the disclosure. Further, since numerous modifications and changes will readily occur to those skilled in the art, it is not desired to limit the disclosed subject matter to the exact construction and operation shown and described, and accordingly, all suitable modifications and equivalents may be resorted to that fall within the scope of the claims.

We claim:

1. An apparatus for removing sulfur-containing compounds from a hydrocarbon liquid, the apparatus comprising:
    at least one tank defining a chamber with a top end and a bottom end, the tank including:
        a gas inlet toward the bottom end of the chamber and through which a gas is introduced into the chamber and a gas outlet toward the top end of the chamber and through which a gas exits the chamber for causing a vertical upward flow of a gas in the chamber between the gas inlet and the gas outlet;
        a fluid inlet toward the top end of the chamber and through which the hydrocarbon fluid is introduced into the chamber and a fluid outlet toward the bottom end and through which the hydrocarbon fluid exits the chamber for causing a vertical downward flow of a fluid in the chamber between the fluid inlet and the fluid outlet;
    a fluid circulation assembly including at least one pump in fluid communication with the fluid inlet of the at least one tank to create a flow of the hydrocarbon liquid into the chamber to descend from the fluid input to the fluid outlet;

a gas circulation assembly including a gas compressor configured to circulate a gas flow along a gas path and from the gas inlet of the tank to the gas outlet of the tank, the gas being predominantly nitrogen (N2) gas, wherein the gas inlet and outlet and the fluid inlet and outlet of the at least one tank are arranged on the tank to create a crossflow of the vertical downward liquid flow and the vertical upward gas flow in the chamber of the tank such that sulfur-containing compounds are transferred from the liquid flow to the gas flow;

a gas processor assembly configured to remove sulfur-containing compounds from the gas flow before recirculating the gas flow through the chamber of the at least one tank;

a barrier in the chamber forming at least a partial barrier to the vertical downward flow of the hydrocarbon liquid and the vertical upward flow of the gas in the chamber to facilitate intermixing of the liquid moving between the fluid inlet and the fluid outlet and the gas moving between the gas inlet and the gas outlet, the barrier being positioned in a vertical arrangement between the gas inlet and the fluid outlet located toward the bottom end of the chamber and the gas outlet and the fluid inlet located toward the top end of the chamber; and wherein the barrier comprises a plurality of baffles.

2. The apparatus of claim 1 wherein the gas outlet is vertically spaced from the gas inlet such that the gas outlet is located at a higher vertical level than the gas inlet to cause the vertical upward gas flow;

wherein the fluid inlet is vertically spaced from the fluid outlet such that the fluid inlet is located at a higher vertical level than the fluid outlet to cause the vertical downward flow of hydrocarbon liquid such that the flow of hydrocarbon fluid is in counterflow to the gas flow.

3. The apparatus of claim 1 wherein at least one tank comprises at least two tanks including a first tank and a second tank, the fluid outlet of the first tank being in fluid communication with the fluid inlet of the second tank such that fluid exiting the chamber of the first tank enters the fluid inlet of the second tank, the gas outlet of the second tank being in fluid communication with the gas inlet of the first tank such that gas exiting the chamber of the second tank enters the gas inlet of the first tank.

4. The apparatus of claim 1 wherein the gas distribution assembly includes a gas distribution manifold located in the chamber of the tank toward the bottom end and being in fluid communication with the gas inlet.

5. The apparatus of claim 1 wherein the gas circulation assembly in a gas source containing a quantity of gas comprising at least 90% nitrogen by volume.

6. The apparatus of claim 1 wherein the gas circulation assembly in a gas source containing a quantity of gas comprising at least 98% nitrogen by volume.

7. The apparatus of claim 1 wherein the gas circulation assembly in a gas source containing a quantity of gas comprising approximately 100% nitrogen by volume.

8. The apparatus of claim 1 wherein the at least one pump of the fluid circulation assembly includes an input pump in in fluid communication with a fluid input of the apparatus and the fluid inlet of the at least one tank.

9. The apparatus of claim 8 wherein the at least one pump of the fluid circulation assembly includes an output pump in fluid communication with the fluid outlet of the at least one tank and a fluid output of the apparatus.

10. The apparatus of claim 9 wherein at least one tank comprises at least two tanks including a first tank and a second tank; and wherein the at least one pump of the fluid circulation assembly includes an intermediate pump in fluid communication with the fluid output of the first tank and with the fluid input of the second tank.

11. A contained system for removing sulfur-containing compounds from a hydrocarbon liquid, the system comprising:

a portable container defining an interior; and an apparatus for removing sulfur-containing compounds from a hydrocarbon liquid entirely contained in the interior of the portable container, the apparatus comprising:

at least one tank defining a chamber with a top end and a bottom end, the tank including:

a gas inlet toward the bottom end of the chamber and through which a gas is introduced into the chamber and a gas outlet toward the top end of the chamber and through which a gas exits the chamber for causing a vertical upward flow of a gas in the chamber between the gas inlet and the gas outlet;

a fluid inlet toward the top end of the chamber and through which the hydrocarbon fluid is introduced into the chamber and a fluid outlet toward the bottom end and through which the hydrocarbon fluid exits the chamber for causing a vertical downward flow of a fluid in the chamber between the fluid inlet and the fluid outlet;

a fluid circulation assembly including at least one pump in fluid communication with the fluid inlet of the at least one tank to create a flow of the hydrocarbon liquid into the chamber to descend from the fluid input to the fluid outlet;

a gas circulation assembly including a gas compressor configured to circulate a gas flow along a gas path and from the gas inlet of the tank to the gas outlet of the tank, the gas being predominantly nitrogen (N2) gas, wherein the gas inlet and outlet and the fluid inlet and outlet of the at least one tank are arranged on the tank to create a crossflow and counterflow of the vertical downward liquid flow and the vertical upward gas flow in the chamber of the tank such that sulfur-containing compounds are transferred from the liquid flow to the gas flow; and a gas processor assembly configured to remove sulfur-containing compounds from the gas flow before recirculating the gas flow through the chamber of the at least one tank;

wherein the at least one tank includes a barrier located in the chamber forming at least a partial barrier to the vertical downward flow of the hydrocarbon liquid and the vertical upward flow of the gas in the chamber to facilitate intermixing of the liquid moving between the fluid inlet and the fluid outlet and the gas moving between the gas inlet and the gas outlet, the barrier being positioned vertically above the gas inlet and the fluid outlet located toward the bottom end of the chamber and vertically below the gas outlet and the fluid inlet located toward the top end of the chamber; and wherein the barrier comprises a plurality of baffles.

* * * * *